United States Patent [19]

Eichler et al.

[11] Patent Number: 4,720,583

[45] Date of Patent: Jan. 19, 1988

[54] PROCESS FOR THE ISOMERIZATION OF O-, M- AND/OR P-TOLUIDINE

[75] Inventors: Klaus Eichler, Eschborn; Ernst I. Leupold, Neu-Anspach; Hans-Jürgen Arpe; Herbert Baltes, both of Frankfurt am Main, all of Fed. Rep. of Germany

[73] Assignee: Hoechst Aktiengesellschaft, Frankfurt am Main, Fed. Rep. of Germany

[21] Appl. No.: 740,238

[22] Filed: May 31, 1985

[30] Foreign Application Priority Data

Jun. 2, 1984 [DE] Fed. Rep. of Germany ....... 3420707

[51] Int. Cl.⁴ ...................... C07C 85/24; C07C 87/56
[52] U.S. Cl. ..................................... 564/305; 564/424
[58] Field of Search ............................... 564/305, 424

[56] References Cited

U.S. PATENT DOCUMENTS

| 4,480,128 | 10/1984 | Arpe et al. | 564/424 |
| 4,650,915 | 3/1987 | Arpe et al. | 570/202 |

FOREIGN PATENT DOCUMENTS

| 0072008 | 2/1983 | European Pat. Off. | 570/202 |
| 0077523 | 4/1983 | European Pat. Off. | |
| 0092103 | 10/1983 | European Pat. Off. | 564/305 |

Primary Examiner—Charles F. Warren
Assistant Examiner—John A. Sopp
Attorney, Agent, or Firm—Curtis, Morris & Safford

[57] ABSTRACT

The invention relates to a process for the isomerization of o-, m- or p-toluidine, or of a mixture of them, on a zirconium-containing zeolite catalyst of the pentasil type. Catalysts of this type are distinguished by particularly high activity and a long useful life. The invention particularly relates to the preparation of m-toluidine by isomerization of o- and/or p-toluidine on zirconium-containing zeolite catalysts of the pentasil type.

9 Claims, No Drawings

PROCESS FOR THE ISOMERIZATION OF O-, M- AND/OR P-TOLUIDINE

The present invention relates to a process for the isomerization of o-, m- and/or p-toluidine on a zeolite catalyst.

o-, m- and p-toluidine (methylanilines, aminotoluenes, tolueneamines), i.e. $C_6H_4CH_3NH_2$ isomers are mostly prepared industrially by reduction of the corresponding nitrotoluenes. In turn, o-, m- and p-nitrotoluene are produced together on nitration of toluene. Thus, for example, under customary conditions of nitration, a mixture of 63% o-, 33–34% p- and 3–4% m-nitrotoluene is obtained, and this can be separated into the pure products by a combination of distillation and crystallization using a special method, called dripping off (Winnacker-Küchler, Carl Hanser Verlag Munich 1972, Volume 4, page 156). The ratio of the isomers can be influenced by a variety of measures (Kirk-Othmer, John Wiley, 3rd Edition, Volume 15, page 929); thus, for example, the proportion by weight of p-nitrotoluene can vary between about 63 and 38%, and that of o-nitrotoluene can vary between 34 and 58%. On the other hand, the proportion of m-nitrotoluene can be varied only to a very limited extent, namely between 2.3 and 4.3% by weight of the total yield of nitrotoluene. Hence there are, in particular, only limited amounts of m-nitrotoluene available for further reduction to m-toluidine.

It has already been disclosed that o-, m- and p-toluidine, or a mixture of them, can be isomerized on zeolite catalysts, zeolites of the pentasil type being preferred (European Pat. No. A1-92103). However, the catalyst described in this patent shows a marked decrease in activity with time, and this is probably due to carbonization. Carbonization of this type is a disadvantage for carrying out an industrial process, since the catalyst must be regenerated frequently.

It has now been found that this decrease in activity is markedly less on isomerization of toluidines on zirconium-containing zeolites of the pentasil type, as are described, for example, in European Pat. No. A2-77,532, and, after an initial brief decrease in the activity, the yields which can be obtained are even completely constant over a long period and are higher than with the catalysts described hitherto.

Thus, the invention relates to a process for the isomerization of o-, m- or p-toluidine, or of a mixture of them, on a zeolite catalyst, which comprises use of a zirconium-containing zeolite of the pentasil type. The present invention particularly relates to a process for the preparation of m-toluidine by isomerization of o- or p-toluidine, or of a mixture of them, on a zeolite of this type.

On the basis of the state of the art, it was surprising and by no means predictable that the isomerization yields obtained on zirconium-containing zeolites of the pentasil type are higher, and the deactivation of the catalyst is less, than with zeolites which contained no zirconium and have previously been described. Comparison of Example 1 with the comparison example shows that, under the same conditions, the isomerization yields obtained with the catalysts according to the invention are considerably higher. Furthermore, no change in the catalytic activity over 120 hours is observed in Example 1, while a marked reduction in activity of the catalysts hitherto known takes place in this period due to catalyst deactivation, as is also shown by the comparison example.

To carry out the process according to the invention, o-, m- or p-toluidine, or a mixture of two or all three of these isomers, is brought into contact with a zirconium-containing zeolite catalyst of the pentasil type. If a mixture which contains all three isomers is used, of course it is only possible to observe an isomerization when the composition of the starting mixture at the reaction temperature is different from that of a toluidine mixture which is in a state of thermodynamic equilibrium. Suitable catalysts are zirconosilicates and zirconoaluminosilicates having the pentasil structure.

In this context, the definition of the term pentasils is that of Kokotailo and Meier ("Pentasil family of high silicon crystalline materials" in Special Publication No. 33 of the Chemical Society, London, 1980). The pentasil family comprises, for example, the synthetic zeolites ZSM-5 (U.S. Pat. No. 3,702,886), ZSM-8 (British Pat. No. 1,334,243), ZSM-11 (U.S. Pat. No. 3,709,979) and ZSM-23 (U.S. Pat. No. 4,076,842).

In the process according to the invention, zirconosilicates and zirconoaluminosilicates with the ZSM-5 structure are particularly suitable, preferably those having the following composition, expressed in molar ratios of the oxides:
$SiO_2$:(0–0.15) $Al_2O_3$:(0.002–1.0) $ZrO_2$, in particular $SiO_2$:(0–0.1) $Al_2O_3$:(0.01–0.4) $ZrO_2$ (see European Pat. No. A2-77,523).

These zirconium-containing zeolites can be prepared by the same methods and using the same organic compounds as have been described for the synthesis of the zeolites ZSM-5 which contain no zirconium, for example using Alkylammonium compounds (U.S. Pat. No. 3,702,886)
Alkylamines (U.S. Pat. No. 4,151,189)
Alkyldiamines (German Offenlegungsschrift No. 2,817,576, German Offenlegungsschrift No. 2,831,334)
Alkylamines in the presence of alkylating agents (European Offenlegungsschrift No. 11,362, German Auslegeschrift No. 2,212,810)
Amino alcohols (British Pat. No. 2,023,562)
Alcohols (German Offenlegungsschrift No. 2,935,123, U.S. Pat. No. 4,175,114, European Offenlegungsschrift No. 42,225, German Offenlegungsschrift No. 2,643,929) and
Ethers (European Offenlegungsschrift No. 51,741).

Preferably, alkylammonium compounds, alkyldiamines, or alkylamines in the presence of alkylating agents are used. Particularly preferred alkylammonium compounds are the tetrapropylammonium compounds, for example the hydroxide or one of the halides. A particularly suitable alkyldiamine is hexamethylenediamine.

For the synthesis of the zirconium-containing pentasils, one or more compounds of the abovementioned classes is mixed with zirconium compounds and with silicon compounds and sodium compounds and water and, in the case of the aluminosilicates, also with aluminum compounds, and this mixture is heated in a closed vessel. In addition, seeding crystals of a pentasil are also preferably added to the mixture before heating.

If tetrapropylammonium compounds are used, the starting compounds are generally used in the following ratio, expressed in molar ratios of the oxides:
$SiO_2$:(0–0.2) $Al_2O_3$:(0.01–1.0) $ZrO_2$:(0.01–0.5) $Na_2O$ :(0.02–1.0) $R_2O$ :(5–100) $H_2O$, preferably in the ratio
$SiO_2$:(0–0.1) $Al_2O_3$:(0.01–0.4) $ZrO_2$:(0.02–0.3) $Na_2O$:(0.03–0.6) $R_2O$:(10–40) $H_2O$,
where R is tetrapropylammonium.

The following are examples of silicon, aluminum, zirconium and sodium compounds which can be used: silica gel, sodium silicate, aluminum hydroxide, aluminum sulfate, sodium aluminate, aluminum halides, aluminum metahydroxide, zirconium halides, zirconium sulfate, zirconyl chloride, sodium hydroxide, sodium sulfate and sodium halides. However, other compounds of the five abovementioned elements are also suitable for the preparation of the zeolites.

The mixture with water of the particular compounds selected is heated in a closed vessel at a temperature between 100° and 200° C., preferably between 130° and 170° C., generally for 18 to 360 hours, preferably 24 to 240 hours.

The zeolites which are formed are isolated in a customary manner, for example by filtration, and are washed and dried.

In the process according to the invention, the zeolites are preferably used in their acid form. These acid forms can be prepared by complete or partial ion exchange by methods known per se from the alkali metal forms, as are a rule produced in the zeolite synthesis or occur as natural products.

An example of a customary method for the preparation of the H form of a zeolite comprises initial conversion of the alkali metal form, by partial or complete ion exchange with an ammonium salt solution, into the ammonium form and subsequent conversion of the latter by calcination into the H form. However, the forms which have been exchanged with alkali metal, alkaline earth metal and rare earth metal ions also show catalytic activity.

The zeolite catalysts according to the invention are generally composed of the catalytically active zeolite component and of a binder material. The latter is necessary in order to convert the zeolite into a physical form suitable for the process according to the invention.

Particularly suitable binder materials are oxides or hydroxides of aluminum and the oxides or hydroxides of silicon, as well as sheet silicates, for example from the kaolin or montmorillonite family.

Before use in the isomerization reaction according to the invention, these zeolite catalysts prepared thus are usually initially activated by calcination at temperatures between 300° and 700° C. It is sometimes advantageous, to improve the stabilization of the catalyst, to carry out the calcination in the presence of steam, ammonia or mixtures of the two.

If the isomerization according to the invention is carried out in the gas phase, a favorable and straightforward procedure for this comprises first passing the toluidine or toluidines from a metering device into a vaporization zone and then passing the resulting gas through a reaction tube which is heated externally and packed with the catalyst. When the isomerization is carried out in the liquid phase, the charge stock is first heated and then passed in the liquid form through the reaction tube which is packed with the catalyst.

It has proved advantageous with regard to the useful life of the catalyst for hydrogen or steam also to be admixed with the charge stock.

Furthermore, it can also be advantageous to admix a carrier gas which is inert under the reaction conditions.

Examples of suitable carrier gases are nitrogen and noble gases.

The amount of hydrogen, steam and/or carrier gas added in the process is such that the residence time is between 1 and 100 s.

It is most advantageous for the hydrogen, steam and/or carrier gas to be mixed with the toluidine or toluidine mixture in the vaporization or heating zone. In this context, it has proved advantageous to heat these gases to the reaction temperature before the mixing.

In general, the isomerization according to the invention is carried out at temperatures between 300° and 550° C., preferably at 320° to 450° C., and under pressures of 0.1 to 30 bar, preferably at 2–20 bar, in particular under atmospheric pressure.

The space velocity of the zeolite catalyst, expressed as LHSV (Liquid Hourly Space Velocity, $h^{-1}$), is generally between 0.05 and 10 $h^{-1}$, preferably between 0.3 and 5 $h^{-1}$.

After leaving the reactor, the reaction products are cooled in order to remove the condensable fractions. However, the isomerization according to the invention is not restricted to this procedure (fixed bed reactor), but can also in principle be carried out in other suitable reactor types (for example fluidized bed reactor).

After removal of the unreacted starting material by distillation, crystallization or adsorption, it can be returned to the reactor.

If the activity of the catalyst decreases with time because of carbonization, it is possible for it to be regenerated. This is carried out by passing oxygen, air, nitrogen/air, oxygen/air, oxygen/inert gas or air/inert gas over the deactivated catalyst at temperatures between 300° and 650° C. Nitrogen/air is preferred for this. During this, the temperature should not exceed 650° C. at any point in the reactor. After the regeneration, the catalyst is again completely active.

Toluidines are important intermediates for the preparation of dyestuffs, vulcanization accelerators, textile auxiliaries and numerous other applications.

The invention is to be illustrated by the Examples which follow, but the Examples are not in any way intended to be restrictive.

EXAMPLES

Example 1

(Isomerization of o-toluidine on a zirconium-containing zeolite of the pentasil type)

(a) Catalyst preparation

A zirconoaluminosilicate of the pentasil type was prepared as in Example 1 of European Pat. No. A2-0,077,523, as follows:

16.6 g of sodium aluminate (54% by weight of $Al_2O_3$, 41% by weight of $Na_2O$) and 14.8 g of sodium hydroxide were dissolved in 200 g of 20% by weight aqueous tetrapropylammonium hydroxide solution (solution A). Another solution (solution B) was prepared by dissolving 620 g of 40% by weight colloidal silica gel in 2,300 g of 20% by weight aqueous tetrapropylammonium hydroxide solution and concentrating this solution in a rotary evaporator to a total of 2,200 g. Solution A and solution B were mixed together. While stirring vigorously, 37.8 g of zirconyl chloride, $ZrOCl_2.8H_2O$, were added to this mixture. The resulting suspension was homogenized and heated at 160° C. in a closed vessel for 120 h. The resulting product was filtered off, washed with water and dried at 120° C. 273 g of zirconoaluminosilicate were obtained. X-ray diffraction analysis showed a product of good crystallinity with the ZSM-5 structure.

The powdered was then calcined for 2 hours at 400° C., 3 h at 450° C. and 8 h at 500° C. in air.

This material had the following composition, expressed in molar ratios of the oxides:
$SiO_2:0.035\ ZrO_2:0.026\ Al_2O_3:0.023\ Na_2O$.

It was treated three times for some hours at 100° C. with 1 molar ammonium nitrate solution, washed, dried and calcined for some hours at 500° C. in air. 65 g of the powder thus obtained were processed with 35 g of $Al_2O_3$ to give pellets of 1.6 mm diameter, and these were calcined at 500° C. for 4 h, reduced to a particle size of 0.25 to 1.0 mm, and calcined at 450° C. in a stream of nitrogen for 2 hours.

(b) Isomerization 15 ml of the catalyst prepared according to (a) were packed into a tube reactor made of glass and of internal diameter 16 mm and length 50 cm, and were covered with glass beads to vaporize the liquid starting material. The temperature in the catalyst bed could be measured using a thermal element which was located in the center of the reactor and was displaceable in the axial direction. The reactor and the vaporization zone were located in an electrically heated oven. 6 ml/h o-toluidine were introduced into the reactor via a metering pump. 1.5 l/h hydrogen were likewise passed over the catalyst via a gas supply comprising reducing valves and devices to measure the pressure and the flow. The condensable reaction products were condensed in a cold trap at 0° C., and were weighed and analyzed by gas chromatography. Table 1 shows the results:

TABLE 1

| Isomerization of o-toluidine on zirconium-containing pentasil | | | | |
|---|---|---|---|---|
| Duration of the experiment (h) | Temperature (°C.) | o-toluidine (% by weight) | m-toluidine (% by weight) | p-toluidine (% by weight) | aniline (% by weight) |
| 5 | 340 | 96.7 | 0.1 | <0.1 | 0.1 |
| 8 | 370 | 86.5 | 10.7 | 1.3 | 0.3 |
| 12 | 400 | 62.5 | 28.7 | 8.1 | 0.6 |
| 20 | 400 | 64.7 | 26.5 | 7.3 | 0.6 |
| 31 | 400 | 69.8 | 25.0 | 6.3 | 0.7 |
| 41 | 400 | 70.0 | 24.0 | 6.1 | 0.6 |
| 48 | 400 | 75.1 | 20.5 | 4.6 | 0.5 |
| 49 | 430 | 37.2 | 45.3 | 15.1 | 1.5 |
| 59 | 430 | 44.9 | 39.1 | 11.8 | 1.1 |
| 74 | 430 | 42.1 | 38.5 | 11.4 | 1.0 |
| 104 | 430 | 47.0 | 37.1 | 10.9 | 0.8 |
| 125 | 430 | 48.5 | 36.9 | 11.2 | 0.8 |
| 190 | 430 | 51.2 | 37.0 | 12.0 | 0.7 |

As is evident from the Table, at 400° C. there was still some deactivation of the catalyst between the 12th and the 48th hour, and at 430° C. there was still slight deactivation between the 49th and the 59th hour, but thereafter up to the 190th hour there was no further decline in activity observed.

Comparison example (Isomerization of o-toluidine on H-ZSM-5)

This isomerization was carried out under the same conditions as in Example 1, but using 15 ml of H-ZSM-5 as the catalyst, the preparation of which is described in, for example, U.S. Pat. No. 3,702,886. Table 2 shows the results:

TABLE 2

| Isomerization of o-toluidine on H—ZSM-5 | | | | |
|---|---|---|---|---|
| Duration of the experiment (h) | Temperature (°C.) | o-toluidine (% by weight) | m-toluidine (% by weight) | p-toluidine (% by weight) | aniline (% by weight) |
| 2 | 370 | 86.0 | 11.1 | 2.9 | 0.5 |
| 9 | 400 | 62.0 | 24.3 | 6.5 | 1.1 |
| 23 | 400 | 66.4 | 19.1 | 4.8 | 1.0 |
| 30 | 400 | 71.0 | 18.2 | 4.8 | 1.0 |
| 44 | 400 | 75.2 | 14.3 | 3.5 | 0.7 |
| 51 | 430 | 52.1 | 31.6 | 9.9 | 1.8 |
| 72 | 430 | 67.2 | 22.0 | 8.8 | 1.4 |
| 100 | 430 | 73.9 | 17.7 | 5.8 | 0.9 |
| 128 | 430 | 80.4 | 13.2 | 4.6 | 0.7 |

Comparison with Example 1 shows that even at 400° C. the yields of m- and p-toluidine were less, but in particular at 430° C. no constant level was reached, the catalyst showing a continous deactivation between the 51st and 128th hour.

EXAMPLE 2

This experiment was carried out with the catalyst already used in Example 1 (without previous regeneration). 15 ml/h p-toluidine and 1.5 l/h hydrogen were passed at 430° C. over the catalyst. After a fore-run time of 15 min to set up constant operating conditions, the condensate was collected for 1 hour. It comprised 14.0% by weight of o-, 56.8% by weight of m- and 26.4% by weight of p-toluidine, as well as 1.2% by weight of aniline.

We claim:

1. A process for the isomerization of o-, m-or p-toluidine, or of a mixture of them, on a zeolite catalyst, which comprises contacting the toluidine or the mixture with a zirconium-containing zeolite of the pentasil type wherein the zeolite is synthesized in the presence of zirconium.

2. The process as claimed in claim 1, wherein the zeolite is in its acid form.

3. A process for the preparation of m-toluidine by isomerization of o- or p-toluidine, or of a mixture of them, on a zeolite catalyst, which comprises contacting the o- or p-toluidine or the mixture with a zirconium-containing zeolite of the pentasil type wherein the zeolite is synthesized in the presence of zirconium.

4. The process as claimed in claim 3, wherein the zeolite is in its acid form.

5. The process as claimed in claim 1, which is carried out at a temperature between 300° and 550° C.

6. The process as claimed in claim 1, which is carried out at a pressure between 0.1 bar and 30 bar.

7. The process as claimed in claim 1, wherein the isomerization is carried out in the presence of hydrogen, nitrogen, steam, argon or of a mixture of these.

8. The process as claimed in claim 3, which is carried out at a temperature between 300° and 550° C.

9. The process as claimed in claim 3, which is carried out at a pressure between 0.1 bar and 30 bar.

* * * * *